(12) United States Patent
Martinez et al.

(10) Patent No.: US 6,582,955 B2
(45) Date of Patent: Jun. 24, 2003

(54) BIOREACTOR WITH APPLICATION AS BLOOD THERAPY DEVICE

(75) Inventors: F. Jesus Martinez, Mission Viejo, CA (US); Virginia Thanh Ta, Garden Grove, CA (US)

(73) Assignee: Spectrum Laboratories, Inc., Rancho Dominguez, CA (US)

( * ) Notice: Subject to any disclaimer, the term of this patent is extended or adjusted under 35 U.S.C. 154(b) by 244 days.

(21) Appl. No.: 09/853,184

(22) Filed: May 11, 2001

(65) Prior Publication Data

US 2002/0168758 A1 Nov. 14, 2002

(51) Int. Cl.⁷ ................................ C12M 1/12
(52) U.S. Cl. ................... 435/297.4; 210/321.8; 210/321.89
(58) Field of Search ............... 210/321.79, 321.8, 210/321.88, 321.89; 435/297.2, 297.4, 299.1; 604/4, 5

(56) References Cited

U.S. PATENT DOCUMENTS

| | | | |
|---|---|---|---|
| 3,883,393 A | 5/1975 | Knazek et al. | |
| 4,184,922 A | 1/1980 | Knazek et al. | |
| 5,015,585 A | 5/1991 | Robinson | |
| 5,064,764 A * | 11/1991 | Besnainon et al. | 435/297.4 |
| 5,290,700 A * | 3/1994 | Binot et al. | 435/297.4 |
| 5,549,674 A * | 8/1996 | Humes et al. | 623/23.65 |
| 5,622,857 A * | 4/1997 | Goffe | 435/378 |
| 5,712,154 A | 1/1998 | Mullon et al. | |
| 5,866,420 A * | 2/1999 | Talbot et al. | 435/395 |
| 5,955,353 A * | 9/1999 | Amiot | 435/297.4 |
| 6,150,164 A * | 11/2000 | Humes | 435/400 |
| 6,242,248 B1 * | 6/2001 | Rozga et al. | 435/297.4 |

* cited by examiner

Primary Examiner—David A. Redding
(74) Attorney, Agent, or Firm—Edgar W. Averill, Jr.

(57) ABSTRACT

A bioreactor having an outer shell compartment containing many coaxial pairs of hollow microporous fibers. An annular compartment exists between an outer surface of the inner hollow microporous fiver and the inner surface of the outer hollow microporous fiber. The annular compartment preferably contains blood or plasma. The blood or plasma is, thus, exposed to two microporous hollow fibers which have fluids which can purify or otherwise affect the blood through the walls of two different microporous hollow fibers. An artificial liver or kidney can result when liver or kidney cells are placed in the shell compartment.

13 Claims, 4 Drawing Sheets

BIOREACTOR WITH APPLICATION AS BLOOD THERAPY DEVICE

FIELD OF INVENTION

The present invention relates generally to the field of biomedicine and biotechnology, and more particularly, to cell-based devices such as bioartificial liver or bioartificial kidney and blood therapy devices such as hemodialysis or hemofiltration system and methods therefore. Although the invention is subject to a wide range of applications, it is especially made suited for use as an extracorporeal blood therapy device with multiple functions integrated in a single module and will be particularly described in that connection.

BACKGROUND OF THE INVENTION

Various reactors, bioreactors, modules and cartridges ("BIOREACTORS") used as cell culture devices and extracorporeal blood therapy devices ["(BIO)ARTIFICIAL ORGANS"] are known. Typically, the known bioreactors utilize hollow-fiber technology. An array of single and dual hollow-fiber reactors exists and their fabrication and application are well known in the prior art as shown by the teachings of U.S. Pat. Nos. 3,442,002; 3,492,698; 3,821,087; 3,883,393, 4,184,922; 4,219,426; 4,220,725; 4,226,378; 4,276,687; 4,283,284; 4,329,229; 4,334,993; 4,361,481; 4,374,802; 4,389,363; 4,647,539; 5,015,585; 5,605,835, 5,712,154 and other related patents.

In a single hollow-fiber bioreactor, a bundle of small-diameter porous hollow fibers are contained in a housing that is rigid and sealed. The bundle of fibers is stretched so that the individual fibers run in parallel to each other. The ends of the bundle are sealed at each end so that two compartments are formed: intrafiber that is within the lumens of the fibers and extrafiber that is outside the fibers but still within the housing. In a dual hollow-fiber bioreactor, two separate bundles of small-diameter porous hollow fibers are contained in a common housing so that three compartments are formed and each compartment has its own inlet and outlet ports.

Applications range from the filtration, purification and reclamation of industrial waste products to highly sophisticated biomedical applications in the Health Sciences Field. These include, but are not limited to, the exchange and mass transfer of dissolved gases and aqueous solutions of typical applications such as hemodialysis, plasma separation, extracorporeal gas exchange, process filtration of pharmaceutical solutions, extracorporeal cell-based artificial organs such as bioartificial livers, and the cultivation and expansion of mammalian and plant cells in bioreactors (U.S. Pat. No. 3,883,393 and other related patents).

The teachings of the above prior art have many shortcomings. The principal shortcoming of single hollow-fiber bioreactor is its inability to perform more than one operation at a time. As result, oxygenation of cells medium has to be provided externally. Moreover, in all hollow-fiber bioreactors (single, dual), mass transport across the fiber wall occurs primarily by diffusion, and the nutrient medium is also the production medium. In addition, the fibers may splay apart from one another when the bundle is sealed in the shell, increasing the possibility that cells between the fibers may be anoxic. The principal drawback of a dual circuit hollow-fiber bioreactor by Knazek et al (U.S. Pat. No. 4,184,922) and by Mullon et al. (U.S. Pat. No. 5,712,154) is that their construction does not guarantee uniform distribution of both sets of fibers (e.g., source or nutrient fibers and sink or production fibers). Cells may preferentially grow on or near the source fibers. In addition, if the second set of fibers is used for bleed-off of concentrated product (sink fibers), the nutrient medium must be oxygenated externally. If, in turn, one of the sets of fibers is used for oxygen delivery, then the nutrient medium is also the production medium, as in a single-fiber module.

A dual hollow-fiber cell culture devices with a tube-within-a-tube configuration had been described by Channing R. Robertson and In Ho Kim in 1985, by Linda Custer in 1988 and by James R. Robinson in 1991 (U.S. Pat. No. 5,015,585). In all instances, the intent of an inventor or author was to place a biological component in annular spaces formed between the inner and outer tubes, to use inner tubes for integrated oxygenation and/or to use them as source or nutrient fibers, and to use the space outside the outer fibers as either a sink or a second passage of fluidized nutrients. Though these devices represented a major improvement, they have certain drawbacks, because when used as a cell culture device or a bioartificial organ, the annular space thickness would have to be relatively thin (on the order of 200 microns as stated in the U.S. Pat. No. 5,015,585) to ensure adequate oxygenation and nutrition of cells. A bioreactor with fiber pairs having such a narrow annular space would have to be very large to accommodate sufficient number of cells to provide enough function. In addition, loading of cells would be very difficult. As a consequence of these drawbacks, none of the aforementioned designs resulted in the development of a commercially viable product.

A need therefore exists for a multi-compartment bioreactor, and a method therefor, that allows integration of at least two functions in a single module and, at the same time, loading and maintenance of large number of viable functional cells.

SUMMARY OF THE INVENTION

The invention, which tends to address this need, resides in a bioreactor. The bioreactor described herein provides advantages over known bioreactors in that it integrates in a single module at least two independent operations (e.g., functions, modes of therapy).

According to the present invention, the foregoing advantage is principally provided by the employment of a three-compartment module whereby the cell (animal, human, plant, insect) can be populated and expanded in an outer (shell) compartment (C1), while circulating a medium (culture medium, blood or plasma) coaxially within the second mid (e.g., annular) compartment (C2) and circulating fluid (e.g., gaseous medium, plasma) within the third inner compartment (C3) adjacent to the C2 compartment. Due to the presence of these three compartments and the proposed method of use thereof, a bioartificial organ (e.g., liver, kidney, pancreas, thyroid, parathyroid, adrenal, etc.) can be constructed, where two different functions (e.g., cell therapy and oxygenation, cell therapy and blood/plasma dialysis or ultrafiltration or diafiltration or any other form of therapy, including regional delivery of pharmacological agents) are integrated in a single module.

In the configuration using hollow fibers, the bioreactor is comprised of a plurality of two hollow fiber bundles, each said hollow fiber bundle interdependent of the other whereby each individual hollow fiber, comprising the plurality of hollow fibers in one bundle, is disposed coaxially inside each hollow fiber of the other hollow fiber bundle. A large number of pairs of hollow fibers are useful such as several hundred pairs.

In accordance with one aspect of this invention, the composite bundle of hollow fibers-within-hollow-fibers is further disposed in a generally rigid, tubular housing having diametrically enlarged double manifolds members adjacent opposite housing ends. Said tubular housing disposes a third compartment enclosing the concentrically arranged fiber-within-a-fiber bundle.

In accordance with another aspect of this invention, relatively resilient plastic sleeve members are carried at each end of each interdependent hollow fiber bundle and the tubular housing; said plastic sleeve members are sealed diametrically opposed to each fiber bundle and the housing member. Preferably, the sleeves are made from a material which sealingly adheres to the each individual hollow fiber and tubular housing to facilitate a hermetic seal of the system. Thus, the three compartments are coaxially disposed yet separate and independent.

In accordance with another aspect of this invention, each of the three compartments has its own inlet and outlet port.

In accordance with another aspect of this invention, the module can be populated with hydrophobic or hydrophilic hollow fibers or a combination thereof.

In accordance with another aspect of this invention, the module can be populated with surface modified membranes for specific applications; for example, membranes with anti-fouling and/or anti-thrombogenic properties with enhanced bio- and/or blood compatibility.

In accordance with another aspect of this invention, it is critical to consider the appropriate spacing (compartment size) between the inner fiber and the concentric outer fiber and the relative size of one hollow fiber to the other and the overall diameter of the tubular housing. The size of the innermost hollow fiber may preferably range from an internal diameter (I.D.) between 100 microns and 1000 microns and a wall thickness of 50 to 100 microns. The axially and concentrically placed outer hollow fiber size would preferably range in size from an internal diameter of 300 microns and a wall thickness of at least 50 microns to an external diameter of 2,000 microns or more. The overall functional surface area (S.A.) of a suitable module will depend on its specific application. The S.A. can range from a few centimeter square to 200 meter square or more. The range of space between OD of inner fiber and ID of outer fiber can range from 50 microns to 1000 microns or more.

It is another aspect of this invention to use one or a combination of hollow fibers with molecular weight cut off's (MWCO) for tailor-made applications (e.g., oxygenation, immunoisolation of cells, collection of substances with specific molecular weights) and/or using one or all of the hollow fiber sizes utilized in the fabrication of a module.

In accordance with another aspect of this invention, the materials used for the inner fiber and/or the outer fiber is preferably a microporous hollow fiber. A preferred range of porosity of from 0.10 microns to 5.0 microns help maintain excellent cell survival, function and proliferation. A 0.2 micron microporous mixed ester cellulose hollow fiber containing bioreactor worked successfully in testing. The use of such microporous hollow fibers allows a greater range of spacing than does the low molecular weight polypropylene suggested in Robinson U.S. Pat. No. 5,015,585.

In accordance with the method of this invention, a bio-artificial liver is constructed where the liver cells are placed in the extrafiber (shell) compartment, the annular space in between the fibers is perfused with whole blood or plasma, and the inner fibers are used for blood purification therapy by means of either dialysis or ultrafiltration or diafiltration.

In accordance with the method of this invention, a bio-artificial liver is constructed where the liver cells are placed in the extrafiber (shell) compartment, the annular space in between the fibers is perfused with whole blood or plasma, and the inner fibers are used for oxygenation of blood/plasma which is pumped through the annular spaces between the two fiber systems.

In accordance with the method of this invention, the fluid circulated through the inner fibers of a bioartificial liver can be a standard hemodialysis fluid, an albumin-enriched solution, a human fresh frozen plasma, or any other suitable fluid.

In accordance with the method of this invention, a bio-artificial kidney is constructed where the renal cells are placed in the extrafiber (shell) compartment, the annular space in between the fibers is perfused with whole blood or plasma, and the inner fibers are used for blood purification therapy by means of either dialysis or ultrafiltration or diafiltration.

In accordance with the method of this invention, the porosity of the inner and outer fiber walls are judiciously chosen so as to use the annular space for passage of blood or plasma and both adjacent compartments for enhanced blood purification therapy, i.e., dialysis, ultrafiltration, diafiltration, drug delivery or any combination thereof. In accordance with this method of the invention, the fluid circulated through the spaces adjacent to the annular space (outer fiber compartment and inner fiber compartment) can be a standard hemodialysis fluid, an albumin enriched solution, a human fresh frozen plasma, or any other suitable fluid. Thus, in accordance with this method of the invention cell therapy is not used at all and the module functions as an interface for two different blood therapies (e.g., hemodialysis and hemodiafiltration).

In accordance with the method of this invention, the porosity of the inner fiber wall in a bioartificial liver is adjusted to specific mode of blood purification therapy, i.e., dialysis, ultrafiltration, or diafiltration.

It is to be understood by those skilled in the art that the above description and general specifications are merely for illustrative purposes and shall in no way limit the range of specifications suitable for use in the three-compartment hollow fiber or flat-bed module.

BRIEF DESCRIPTION OF THE DRAWINGS

FIG. 5 is a cross-sectional view taken along 5—5 of FIG. 4.

FIG. 6 is a cross-sectional view of an alternate embodiment of the bioreactor of FIG. 1.

DESCRIPTION OF THE PREFERRED EMBODIMENTS

Figure 1:
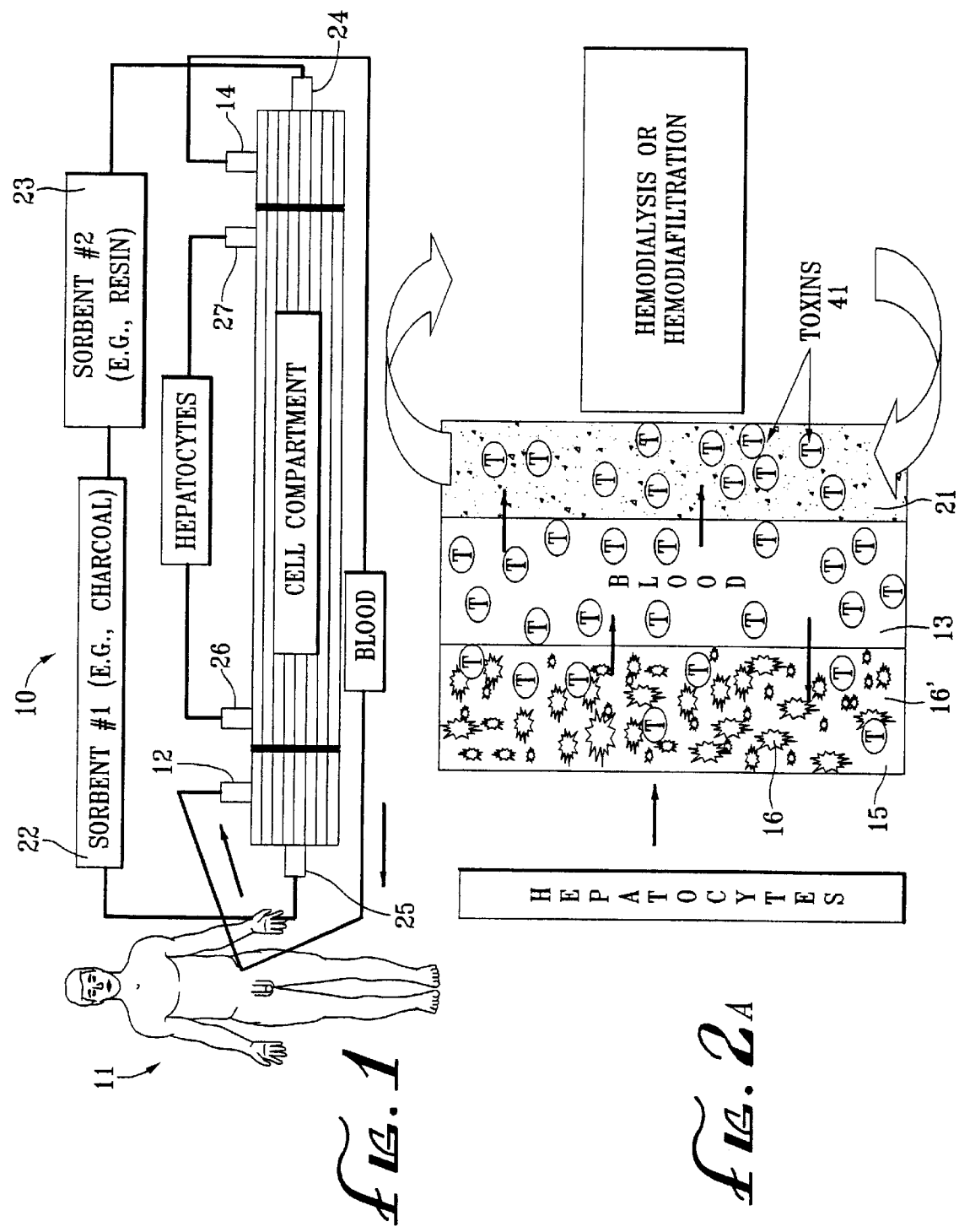
FIG. 1 is a diagrammatic view showing the extracorporeal blood therapy device of the present invention adjacent a patient.
Figure 2:
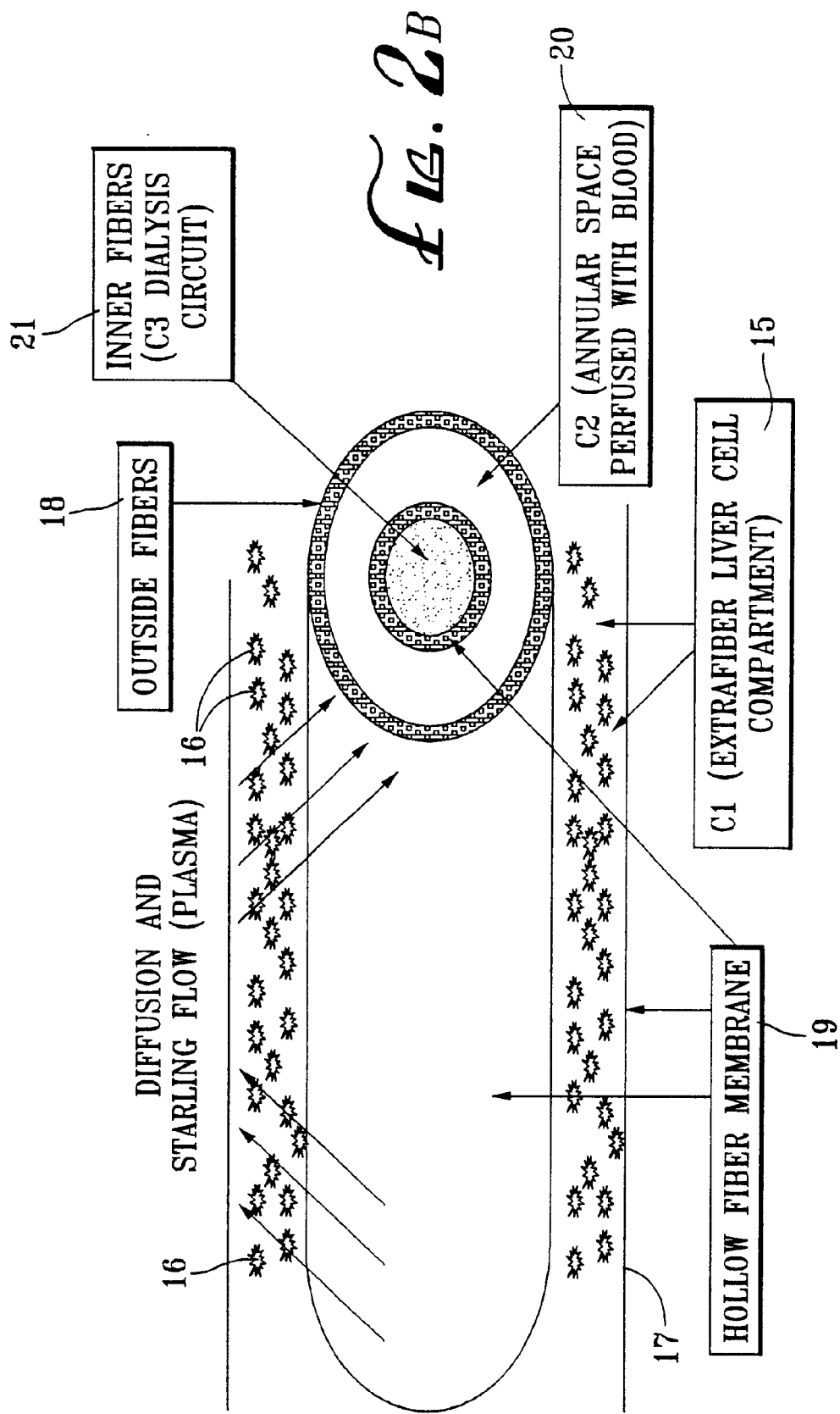
FIG. 2A is a diagrammatic view of the process of the blood therapy device of FIG. 1.
FIG. 2B is a diagrammatic perspective view of a pair of concentrically oriented fibers within the casing of the blood therapy device of FIG. 1.

The extracorporeal blood therapy device or bioreactor 10 of the present invention is shown in diagrammatic view in FIG. 1 where it is shown treating the blood of a patient 11. The bioreactor 10 could function as a bioartificial liver where the blood is circulated into inlet port 12. The blood 13 passes through the bioreactor and out of blood exit port 14 and back to patient 11. As shown best in FIG. 2B of the drawings, the outer shell compartment 15 would contain liver cells 16. Outer shell compartment 15 is bound by outer shell 17 and the outer surface of outside fiber 18. Concentrically positioned within outside fiber 18 is the annular space 20 between inner hollow fiber membrane 19 and outside fiber 18 is perfused with blood 13. Within inner hollow fiber membrane 19 is a passageway for a hemodialysis fluid 21. This stream may also be treated with other materials such as sorbent 22 shown in FIG. 1 such as charcoal, or sorbent 23 such as a resin. Fluid 21 passes into bioreactor 10 through inlet port 24 and out through outlet port 25 preferably in a countercurrent manner with respect to the flow of fluid in annular space 20. The hepatocytes 15 are inoculated into a shell compartment 15 via port 26 and port 27. The hepatocytes preferably do not circulate as they are injected into C3 compartment which sealed during therapy.

Figure 3:
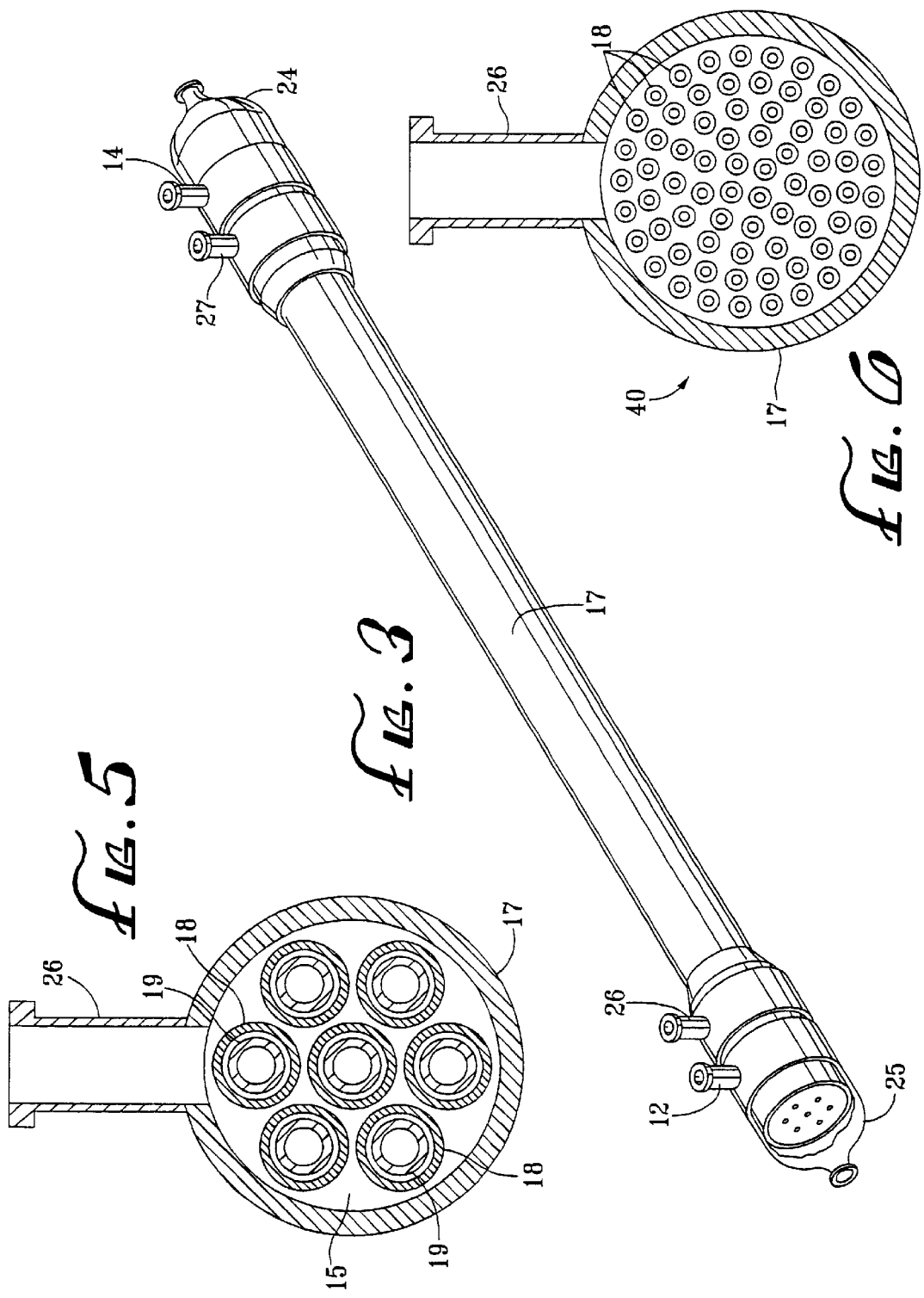
FIG. 3 is a perspective view of the bioreactor of FIG. 1.
Figure 4:
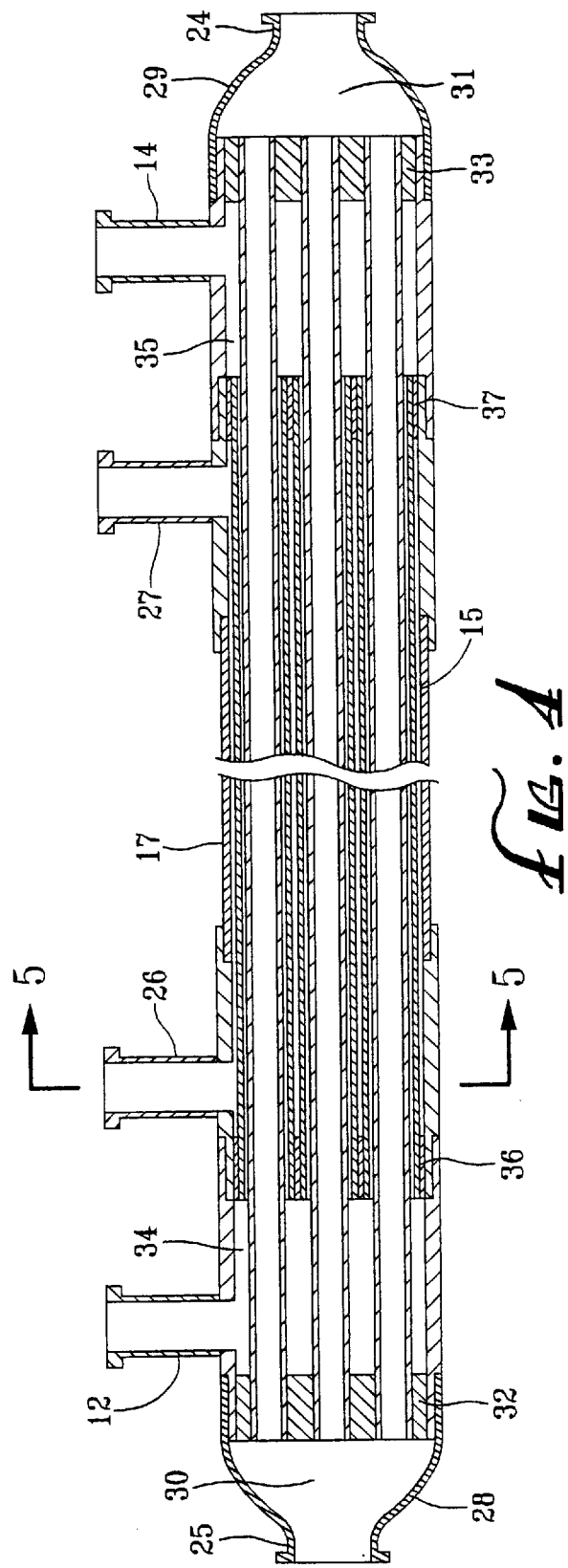
FIG. 4 is a cross-sectional view of the bioreactor of FIG. 3.

A particular construction of a multi-fiber bioreactor is shown in FIGS. 3, 4 and 5 where seven sets of dual fibers are shown within shell 17 and end manifold 28 is connected at one end of the bioreactor as shown in FIG. 4, and a second end manifold 29 is connected at the other end. While seven sets of dual fibers are shown in FIG. 4 for use as an artificial liver, it is preferable to have at least one hundred pairs of fibers and several hundred is still further preferred. As can be seen best in FIG. 4, the inner fiber circuit has an outlet manifold area 30 for the inner fibers and an inlet manifold area 31 for the inner fibers. This is bounded by sealant rings 32 and 33, respectively, which are preferably fabricated from polyurethane or epoxy resins. Sealant rings 32 and 33 provide a barrier between fluid in the inner fiber and the fluid in the annular space, which is within annular space manifold 34 and 35, respectively. A pair of inner sealant rings 36 and 37, also preferably fabricated from polyurethane or epoxy resins, provide a barrier between the annular space manifolds 34 and 35 and the outer shell compartment 15.

FIG. 6 shows a bioreactor 40 which has a large number of pairs of coaxially aligned fibers 18 and 19. The number of fibers can thus preferably range between one hundred and several thousand, depending on the specific application and need for specific level of function, with 100 to 1,000 being preferred.

An important feature of the present invention is the provision of passing blood through the annular space 20. Thus, the width of the annular space is critical and should be between 100 and 1000 microns, and preferably about 250 microns. By passing blood or plasma through the annular space, it can be treated with either cells and another fluid or with two separate fluids at the same time. As shown diagrammatically in FIG. 2A, toxins 41 can pass from the blood into the fluid 21 in the inner fibers and into the outer shell compartment 15 where they can be processed by the viable cells such as hepatocytes or can be removed through another dialysis, ultrafiltration or diafiltration fluid 16 if the shell compartment 15 is used for additional blood purification (e.g., sorption) therapy. Thus, the annular space 20 can be surrounded by two separate blood purification fluids. In addition to the above-mentioned blood purification fluids, fluids containing soluble factors to be delivered to the patient's blood or plasma may be used as additional blood purification fluids.

The materials from which the fibers are fabricated are related to the desired function. For instance, when a bioartificial liver is used, the inner fiber would preferably function with a dialysis fluid and be fabricated from several homopolymers or co-polymers, but preferably from polysulfone and the outer fiber would contain a similar or dissimilar polymeric microporous hollow fiber membrane and an antifouling coating along its outer surface.

When a bioartificial kidney is constructed, renal cells are placed in the shell compartment and the inner fiber would contain either dialysis or ultrafiltration or diafiltration fluids.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

We claim:

1. A bioreactor comprising a three component module comprising:
   an outer shell having an inner surface defining the outer wall of an outer shell compartment, said outer shell compartment having an entry port and an exit port;
   at least one hundred outside fibers positioned within said outer shell compartment, said outside fibers having an outer surface exposed to said outer shell compartment and defining a cell containing compartment between said inner surface of said outer shell and said outer surface of said at least one hundred outside fibers and said at least one hundred outside fibers, each having an inner wall surrounding an outside fiber lumen and defining an outer wall of an annular compartment, said annular compartment sealed from said outer shell compartment and connected to an annular compartment manifold set having an annular compartment inlet port and an annular compartment outlet port;
   at least one inner fiber positioned within said outside fiber lumen and said at least one inner fiber having an outer wall surface defining an inner wall of said annular compartment and said at least one inner fiber having an inner wall surrounding an inner fiber lumen forming an inner compartment, said inner compartment sealed from said annular compartment and said outer shell compartment and said inner compartment being connected to an inner compartment manifold set having an inner compartment inlet port and an inner compartment outlet port; and
   wherein said outer shell compartment contains cells in a liquid medium, said annular compartment contains a circulating plasma containing perfusate and said inner compartment contains a different nutrient medium whereby a bioartificial organ can be operating carrying out two different functions.

2. The bioreactor of claim 1 wherein said bioreactor has a single outer shell surrounding a plurality of fiber pairs arranged in a fiber-within-a-fiber configuration.

3. The bioreactor of claim 2 wherein said outer shell is formed from a rigid material and has a pair of diametrically enlarged double manifold members adjacent opposite housing ends, each diametrically enlarged double manifold comprising an outermost manifold connected to said inner compartment manifold and a mid-manifold inwardly spaced from said outermost manifold and connected to said annular compartment manifold.

4. The bioreactor of claim 3 wherein said each of said outermost manifolds is formed between said outer shell and an outer resilient polymeric sleeve member sealingly surrounding said outer wall surface of said at least one inner fiber.

5. The bioreactor of claim 4 wherein said each of said mid-manifolds is formed between outer resilient polymeric sleeve member and an inner resilient polymeric sleeve member which sealingly surrounds said outer surface of each of said at least one hundred outside fibers.

6. The bioreactor of claim 1 wherein each of said at least one hundred outside fibers is fabricated from a hydrophobic polymer.

7. The bioreactor of claim 1 wherein said at least one inner fiber is fabricated from a hydrophobic polymer.

8. The bioreactor of claim 1 wherein each of said at least one hundred outside fibers is fabricated from a hydrophilic polymer.

9. The bioreactor of claim 1 wherein said at least one inner fiber is fabricated from a hydrophilic polymer.

10. The bioreactor of claim 1 wherein said at least one inner fiber has an internal diameter between 100 and 1,000 microns and a wall thickness of from 50 to 100 microns.

11. The bioreactor of claim 10 wherein each of said at least one hundred outside fibers has an internal diameter of at least 300 microns, a wall thickness of at least 50 microns and an external diameter of at least 2,000 microns.

12. A bioartificial liver comprising a three component module comprising:

an outer shell having an inner surface defining the outer wall of an outer shell compartment, said outer shell compartment having an entry port and an exit port and said outer shell compartment containing liver cells;

at least 100 outside fibers positioned within said outer shell compartment, said outside fibers having an outer surface exposed to said outer shell compartment and defining a cell containing compartment between said inner surface of said outer shell and said outer surface of said at least one hundred outside fibers and said at least one hundred outside fibers, each having an inner wall surrounding an outside fiber lumen and defining an outer wall of an annular compartment, said annular compartment sealed from said outer shell compartment and connected to an annular compartment manifold set having annular compartment inlet port and an annular compartment outlet port and said annular compartment is perfused with whole blood or plasma; and an inner fiber positioned within each of said at least one hundred outside fibers lumen and said inner fiber having an outer wall surface defining an inner wall of said annular compartment and said inner fiber having an inner wall surrounding an inner fiber lumen forming an inner compartment, said inner compartment sealed from said annular compartment and said outer shell compartment and said inner compartment being connected to an inner compartment manifold set having an inner compartment inlet port and an inner compartment outlet port and said inner compartment being used for blood purification therapy by means of either dialysis or ultrafiltration or diafiltration.

13. A bioartificial kidney comprising a three component module comprising:

an outer shell having an inner surface defining the outer wall of an outer shell compartment, said outer shell compartment having an entry port and an exit port, said outer shell compartment containing renal cells;

a plurality of outside fibers positioned within said outer shell compartment, said plurality of outside fibers having an outer surface exposed to said outer shell compartment and defining a cell containing compartment between said inner surface of said outer shell and said outer surface of said plurality of outside fibers and said plurality of outside fibers having an inner wall surrounding an outside fiber lumen and defining an outer wall of an annular compartment, said annular compartment sealed from said outer shell compartment and connected to an annular compartment manifold set having an annular compartment inlet port and an annular compartment outlet port and said annular compartment is perfused with whole blood or plasma; and an inner fiber positioned within each of said plurality of outside fiber lumen and said inner fiber having an outer wall surface defining an inner wall of said annular compartment and said inner fiber having an inner wall surrounding an inner fiber lumen forming an inner compartment, said inner compartment sealed from said annular compartment and said outer shell compartment and said inner compartment being connected to an inner compartment manifold set having an inner compartment inlet port and an inner compartment outlet port and said inner compartment being used for blood purification by means of dialysis or ultrafiltration or diafiltration.

* * * * *